United States Patent [19]

Sugawara et al.

[11] Patent Number: 5,688,493

[45] Date of Patent: Nov. 18, 1997

[54] COSMETIC COMPOSITION FORMULATED WITH AN AQUEOUS POLYMER EMULSION

[75] Inventors: Tooru Sugawara, Chiba; Hitoshi Hosokawa; Koichi Nakamura, both of Funabashi; Michitaka Sawada; Takehiro Tsutsumi, both of Wakayama, all of Japan

[73] Assignee: Kao Corporation, Tokyo, Japan

[21] Appl. No.: 323,578

[22] Filed: Oct. 17, 1994

Related U.S. Application Data

[63] Continuation of Ser. No. 53,204, Apr. 28, 1993, abandoned.

[30] Foreign Application Priority Data

| May 1, 1992 | [JP] | Japan | 4-112860 |
| Feb. 8, 1993 | [JP] | Japan | 5-020112 |

[51] Int. Cl.$^6$ .............................. A61K 7/02; A61K 7/04
[52] U.S. Cl. .............................. 424/61; 424/489
[58] Field of Search .............................. 424/61, 401, 489; 514/772.4, 772.5, 772.6, 844, 937

[56] References Cited

U.S. PATENT DOCUMENTS

| 3,763,073 | 10/1973 | Knutson. | |
| 3,867,331 | 2/1975 | Mikoflavy et al. | 524/748 |
| 4,158,053 | 6/1979 | Greene et al. | 424/61 |
| 4,375,441 | 3/1983 | Adams et al. | 264/25 |
| 4,423,031 | 12/1983 | Murui et al. | |
| 4,747,419 | 5/1988 | Flynn et al. | 401/206 |
| 5,102,654 | 4/1992 | Castrogiovanni et al. | 514/938 |

FOREIGN PATENT DOCUMENTS 0 424 112  4/1991  European Pat. Off. .

*Primary Examiner*—Jeffrey C. Mullis
*Attorney, Agent, or Firm*—Oblon, Spivak, McClelland, Maier & Neustadt, P.C.

[57] ABSTRACT

A cosmetic composition comprising an aqueous polymer emulsion in an amount of from 1 to 60% by weight in terms of the weight of solid contents of the cosmetic composition. The aqueous polymer emulsion is produced by polymerizing at least one polymerizable monomer having a double bond in the presence of a plasticizer or a film-forming auxiliary. This aqueous polymer emulsion ensures in the cosmetic composition excellent gloss, film stability, water repellency, and film-forming properties, and also ensures freedom from cosmetic crumbling due to sweat and sebum.

16 Claims, No Drawings

COSMETIC COMPOSITION FORMULATED WITH AN AQUEOUS POLYMER EMULSION

This application is a Continuation of application Ser. No. 08/053,204, filed on Apr. 28, 1993, now abandoned.

BACKGROUND OF THE INVENTION

1. Field of the Invention

The present invention relates to aqueous polymer emulsions and more particularly to cosmetic compositions formulated therewith. The aqueous polymer emulsions provide a cosmetic composition with exceptional gloss, water-repellency, and film-forming properties.

2. Discussion of the Background

Conventional cosmetic compositions, such as for the hair or skin, are either water- or oil-based, and may contain a very large variety of additional ingredients. These include medicaments, abrasives, colorants, cleaners, and perfumes. To this end, see *Kirk-Othmer, Encyclopedia of Chemical Technology*, Third Edition, Vol. 7, pp. 143–176, hereby incorporated by reference.

A water soluble or oil soluble film-forming polymer is typically blended into cosmetic compositions. When a water soluble polymer is used, the cosmetic composition, after application thereof, is likely to be removed, e.g. by sweat, because of the poor water-resistance of the polymer. Conversely, when an oil soluble polymer is used, the cosmetic composition, after application thereof, is likely to be removed by sebum. These phenomena are known as cosmetic crumbling.

Various attempts have been made to overcome these problems. For instance, cosmetic compositions containing aqueous polymer emulsions have been tried. However, such conventional compositions suffer from an unsatisfactory gloss, inadequate film-forming properties, poor water-repellency, and/or storage instability (Japanese patent "kokoku" publication No. 60-9692 (Shiseido)). The development of various cosmetic compositions containing aqueous polymer emulsions which are outstanding in all of the aforementioned characteristics is therefore desired.

SUMMARY OF THE INVENTION

Accordingly, one object of the present invention is to provide an aqueous polymer emulsion produced by polymerizing a monomer having a polymerizable double bond in the presence of a plasticizer or a film-forming auxiliary, which ensures excellent film-forming performance in a cosmetic composition formulated therefrom.

Another object is to provide a cosmetic composition containing the aforementioned aqueous polymer emulsion which has an excellent gloss, exceptional film-forming properties, avoids cosmetic crumbling and has prolonged storage stability.

The foregoing and other objects, features, and advantages of the present invention will become apparent from the following detailed description and appended claims.

DETAILED DESCRIPTION OF THE INVENTION

Essentially, according to the present invention, there is provided a cosmetic composition comprising an aqueous polymer emulsion in an amount of from 1 to 60 wt % (as a solid content) based on the weight of the whole cosmetic composition.

The aqueous polymer emulsion is produced by polymerizing at least one monomer having a polymerizable double bond in the presence of a plasticizer or a film-forming auxiliary.

The terminology "aqueous polymer emulsion" used herein means an emulsion including a solvent comprising water and, dispersed therein, a polymer. The polymer comprises the solid contents of the aqueous polymer emulsion. Preferably the solvent comprises at least 35% by volume water. More preferably, the solid content of the aqueous polymer emulsion is 25–65% by weight, still more preferably 35–55% by weight.

The monomer having a polymerizable double bond for use in the present invention may be a hydrophilic monomer or a hydrophobic monomer.

Representative examples of hydrophilic monomers include ethylenically unsaturated carboxylic acids, such as acrylic acid, methacrylic acid, itaconic acid, maleic acid, fumaric acid and crotonic acid; hydroxyl group-containing ethylenic monomers, such as hydroxyethyl acrylate, hydroxyethyl methacrylate, glycidyl acrylate, glycidyl methacrylate, ethylene glycol diacrylate, ethylene glycol dimethacrylate, polyethylene glycol monoacrylate, and polyethylene glycol monomethacrylate; ethylenic amides, such as acrylamide, methacrylamide, N-methylolacrylamide, N-methylolmethacrylamide and N-diacetonacrylamide; and ethylenic amines or salts thereof, such as aminoethyl acrylate, aminoethyl methacrylate, N,N-dimethylaminoethyl acrylate, N,N-dimethylaminoethyl methacrylate, N,N-diethylaminoethyl acrylate, N,N-diethylaminoethyl methacrylate, N,N,N-trimethylaminoethyl acrylate, and N,N,N-trimethylaminoethyl methacrylate.

Representative examples of hydrophobic monomers include aromatic mono- or divinyl compounds, such as styrene, α-methylstyrene, chlorostyrene, alkylstyrene and divinylbenzene; acrylates and methacrylates, such as methyl acrylate, methyl methacrylate, ethyl acrylate, ethyl methacrylate, propyl acrylate, propyl methacrylate, butyl acrylate, butyl methacrylate, 2-ethylhexyl acrylate, 2-ethylhexyl methacrylate, tert-butyl acrylate, tert-butyl methacrylate, cyclohexyl acrylate and cyclohexyl methacrylate; vinyl cyanide compounds, such as acrylonitrile and methacrylonitrile; vinyl esters, such as vinyl acetate; vinyl halides, such as vinyl chloride and vinylidene chloride; ethylenically unsaturated fluoromonomers, such as trifluoroethyl methacrylate, 2,2,3,3-tetrafluoropropyl methacrylate, 2,2,3,3,4,4-hexafluorobutyl methacrylate, perfluorooctyl methacrylate and perfluorooctyl acrylate; and ethylenically unsaturated silicone macromonomers (i.e. polysilicones), such as represented by the following formulae (1), (2), (3), (4), and (5):

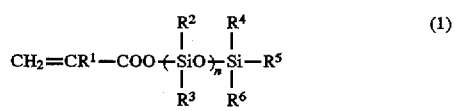

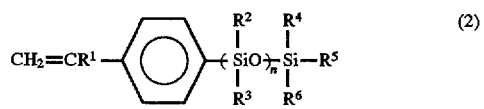

-continued

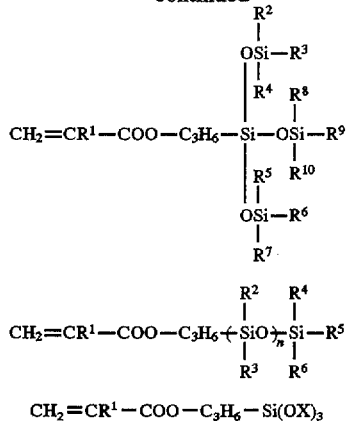

$$CH_2=CR^1-COO-C_3H_6-Si(OX)_3 \quad (5)$$

In the above formulae, $R^1$ represents a hydrogen atom or a methyl group; each of $R^2$-$R^{10}$ represents a lower alkyl group, a lover alkoxy group or a phenyl group ("lower" being $C_1$-$C_6$, preferably $C_1$-$C_5$, more preferably $C_1$-$C_4$); X represents a group of the following formula:

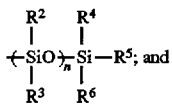

n is an integer of from 1 to 500.

Only one monomer may be used, or two or more monomers may be used in combination. It is generally preferred to employ a mixture of from 0.01 to 30% of a hydrophilic monomer and from 70 to 99.99% of a hydrophobic monomer, and more preferred to employ a mixture of from 0.01 to 15% of a hydrophilic monomer and from 85 to 99.99% of a hydrophobic monomer.

Representative examples of plasticizers or film-forming auxiliaries suitable for use in the present invention include cellosolves, such as cellosolve, methyl cellosolve and butyl cellosolve; carbitols, such as carbitol, dimethylcarbitol, diethylcarbitol, butylcarbitol and dibutylcarbitol; carbonates, such as ethylene carbonate and propylene carbonate; acetates, such as cellosolve acetate, butyl cellosolve acetate, butylcarbitol acetate and sucrose acetate; alcohols, such as hexanol, benzyl alcohol and phenethyl alcohol; diols, such as hexylene glycol, ethylene glycol and propylene glycol; esters, such as phthalic diesters, adipic diesters, succinic diesters, sebacic diesters, abietic esters, caprylic esters, caproic esters, acetic esters, enanthic esters, myristic esters and citric esters; benzoic esters, such as sucrose benzoate; and diethylbenzene.

The plasticizer or film-forming auxiliary is preferably added in an amount of from 1 to 50 parts by weight, more preferably from 5 to 30 parts by weight, per 100 parts by weight of the monomer from the viewpoint of polymerization stability, storage stability, and water repellency and durability of a produced film.

The aqueous polymer emulsion for use in the present invention is obtained by polymerizing the monomer in the presence of the plasticizer or film-forming auxiliary. According to desired use, the plasticizer or film-forming auxiliary may further be added to the produced aqueous polymer emulsion, i.e., the percent solids content may be adjusted in this manner or by addition of solvent. The solid content may also be adjusted by removal of solids, e.g., when the polymer is produced by emulsion polymerization.

In the polymerization, a polymerization initiator is generally added. The polymerization initiator is not particularly limited, and includes for example, organic polymerization initiators inclusive of hydroperoxides, such as cumene hydroperoxide, diisopropylbenzene hydroperoxide and paramenthane hydroperoxide; peroxides, such as benzoyl peroxide and lauroyl peroxide; and azo compounds, such as azobisisobutylonitrile, and inorganic polymerization initiators inclusive of persulfates, such as potassium persulfate, sodium persulfate and ammonium persulfate. Moreover, a redox polymerization initiator may be used in combination with a reducing agent, such as sodium bisulfite, ascorbic acid and salts thereof.

In the polymerization, further, a surfactant is preferably added for ensuring dispersion stability.

The surfactant for use in the present invention is not particularly limited, and includes anionic, cationic and nonionic surfactants. These surfactants may be used in combination. For example, a mixture of an anionic surfactant and a nonionic surfactant or a mixture of a cationic surfactant and a nonionic surfactant may be used in the present invention.

Representative examples of nonionic surfactants include polyethylene oxide alkyl ethers, polyethylene oxide alkylphenyl ethers and polyethylene oxide—polypropylene oxide block copolymers. Representative examples of anionic surfactants include alkylbenzene sulfonates, alkylnaphthalene sulfonates and polyethylene oxide alkyl ether sulfates. Representative examples of cationic surfactants include primary, secondary and tertiary amine salts and quaternary ammonium salts having an aliphatic hydrocarbon residue.

The surfactant is preferably added in an amount of up to 5 parts by weight, more preferably up to 3 parts by weight per 100 parts by weight of the monomer. When the amount of added surfactant exceeds 5 parts by weight, film properties and film adhesion are likely to become poor.

In the polymerization of the monomer, a chain transfer agent may be added. Representative examples of chain transfer agents include mercaptans, such as octyl mercaptan, n-dodecyl mercaptan, t-dodecyl mercaptan, n-hexadecyl mercaptan, n-tetradecyl mercaptan and t-tetradecyl mercaptan; xanthogen disulfides, such as dimethylxanthogen disulfide, diethylxanthogen disulfide and diisopropylxanthogen disulfide; thiuram disulfides, such as tetramethylthiuram disulfide, tetraethylthiuram disulfide and tetrabutylthiuram disulfide; halogenated hydrocarbons, such as carbon tetrachloride and ethylene bromide; hydrocarbons, such as pentaphenylethane; unsaturated cyclic hydrocarbon compounds, such as acrolein, methacrolein, allyl alcohol, 2-ethylhexyl thioglycolate, turbinolene, α-terpinene, gamma-terpinene, dipentene, a-methylstyrene dimer (preferably containing at least 50 parts by weight of 2-4-diphenyl-4-methyl-1-pentene), 9,10-dihydroanthracene, 1,4-dihydronaphthalene, indene and 1,4-cyclohexadiene; and unsaturated heterocyclic compounds, such as xanthene and 2,5-dihydrofuran. These may be used either alone, or in combination.

In the present invention, the polymerization of the monomer is conducted according to the conventional polymerization techniques, such as emulsion polymerization, solution polymerization, bulk polymerization, precipitation polymerization or soap-free polymerization. The solid content of the aqueous polymer emulsion can then be adjusted in the manner previously mentioned.

The polymer of the aqueous polymer emulsion produced by the above described polymerization preferably has a weight average molecular weight of 10,000 to 200,000, more preferably in the range of from 10,000 to 100,000, even more preferably 20,000 to 80,000, still more preferably 25,000–60,000.

Either only one aqueous polymer emulsion or two or more aqueous polymer emulsions may be blended into the cosmetic composition of the present invention. When two or more aqueous polymer emulsions are blended into the cosmetic composition, the blending may be effected so as to combine two or more polymers respectively having different glass transition temperatures or different average molecular weight.

The aqueous polymer emulsion is blended as a film-forming base material into the cosmetic composition of the present invention in an amount of from 1 to 60% by weight (below referred to simply as "%") relative to the weight of the whole cosmetic composition, in terms of the weight of solid contents. When the amount is less than 1%, the effect of the present invention cannot be attained. On the other hand, when the amount exceeds 60%, the viscosity of the cosmetic composition is so high that it becomes difficult to prepare cosmetics and apply the resultant cosmetics to the skin and hair.

In addition to the above components, other components generally used as a cosmetic component, such as an oil, a humectant, an ultraviolet absorbing agent, a chelating agent, a pH control agent, an antiseptic, a thickener, a dye, a pigment and a perfume, may be blended into the cosmetic composition of the present invention, as long as the effect of the present invention is not adversely affected. The cosmetic composition of the present invention can be formulated into various cosmetic forms according to conventional methods. See, generally, *Kirk-Othmer*, ibid., for useful additives and cosmetic forms.

As a humectant, use is made of, for example, ethylene glycol, diethylene glycol, triethylene glycol and polyethylene glycols higher than tri; propylene glycol, dipropylene glycol and polypropylene glycols higher than tri; butylene glycols such as 1,3-butylene glycol and 1,4-butylene glycol; polyglycerols such as glycerol, diglycerol and polyglycerols higher than di; sugaralcols such as sorbitol, mannitol, xylitol and maltitol; ethylene oxide (hereinafter referred to as EO) and propylene oxide (hereinafter referred to as PO) adducts of glycerols; EO and PO adducts of sugaralcohols; monosaccharides such as galactose and fructose, and their EO and PO adducts; polysaccharides such as maltose and lactose, and their EO and PO adducts; sodium pyrrolidone carboxylate, polyoxyethylene methyl glucosides (mols of added EO=10, 20, etc.), basic amino acids and urea. These humentants provide the skin with moistness when incorporated in amounts of 0.01 to 30%, and especially 0.1 to 10%.

As a pigment, use is made of an organic pigment, such as 12120, 73360, 74160 and 11680 (Color Index, CI), or an inorganic pigment, such as titanium dioxide, brown iron oxide, red iron oxide, mica titanium and bismuth oxychloride.

A dispersant for such a pigment may also be incorporated in the cosmetic composition of the present invention, which includes an anionic surfactant, such as soap, zinc laurate, zinc myristate, magnesium myristate, zinc palmitate, magnesium stearate, zinc stearate, aluminum stearate, calcium stearate, sodium lauryl sulfate, triethanolamine lauryl sulfate, sodium cetyl sulfate, triethanolamine polyoxyethylene lauryl ether sulfate, sodium polyoxyethylene lauryl ether sulfate, polyoxyethylene lauryl ether phosphoric acid, sodium polyoxyethylene lauryl ether phosphate, polyoxyethylene cetyl ether phosphoric acid, sodium polyoxyethylene cetyl ether phosphate, polyoxyethylene stearyl ether phosphoric acid, polyoxyethylene oleyl ether phosphoric acid, sodium polyoxyethylene oleyl ether phosphate, polyoxyethylene alkylphenyl ether phosphoric acid, triethanolamine polyoxyethylene alkylphenyl ether phosphate, sodium polyoxyethylene alkylphenyl ether phosphate, lauroylsarcosine sodium salt and soybean phospholipid. Further, the pigment dispersant includes a cationic surfactant, such as stearyltrimethylammonium chloride, distearyldimethylammonium chloride, benzalkonium chloride, benzethonium chloride, stearyldimethylbenzylammonium chloride, cetylpyridinium chloride, alkylisoquinolinium bromide and domiphene bromide.

Still further, the pigment dispersant may include an amphoteric surfactant, such as sodium β-laurylaminopropionate, betaine lauryldimethylaminosulfate and 2-alkyl-N-carboxymethyl-N-hydroxyethylimidazolinium betaine.

The pigment dispersant may also include a nonionic surfactant, such as self-emulsifiable glycerol monostearate, lipophilic glycerol monostearate, lipophilic glycerol monooleate, ethylene glycol monostearate, propylene glycol monostearate, propylene glycol dioleate, sorbitan monolaurate, sorbitan monopalmitate, sorbitan monostearate, sorbitan monooleate, sorbitan sesquioleate, sorbitan trioleate, sucrose fatty acid esters, undecylenic acid monoethanolamide, lauric acid diethanolamide, coconut oil fatty acid diethanolamide, polyethylene glycol monolaurate, polyethylene glycol monostearate, polyethylene glycol monooleate, myristyl lactate, cetyl lactate, polyoxyethylene lauryl ether, polyoxyethylene cetyl ether, polyoxyethylene stearyl ether, polyoxyethylene oleyl ether, polyoxyethylene octylphenyl ether, polyoxyethylene nonylphenyl ether, polyoxyethylene stearic acid amide, polyoxyethylene glycerol monostearate, polyoxyethylene sorbitol monolaurate, polyoxyethylene sorbitan monolaurate (20EO), polyoxyethylene sorbitan monopalmitate (20EO), polyoxyethylene sorbitan monostearate (6EO), polyoxyethylene sorbitan monostearate (20EO), polyoxyethylene sorbitol hexastearate, polyoxyethylene sorbitan monooleate (20EO), polyoxyethylene sorbitan trioleate (20EO), polyoxyethylene sorbitol tetraoleate, polyoxyethylene sorbitol beeswax, polyoxyethylene castor oil, polyoxyethylene hardened castor oil and polyoxyethylene lanolin.

As the thickener, use is made of an organic thickener, such as polyvinyl alcohol, polyvinylpyrrolidone, polyacrylamide, polyethylene oxide, methyl cellulose, hydroxyethyl cellulose, cationated guar gum and cationated cellulose, an inorganic bentonite thickener and a water-containing oxide, such as boehmite.

A cosmetic composition formulated with the aqueous emulsion of the present invention, after application thereof to the skin and hair, exhibits exceptional gloss, excellent film stability, water repellency, and film-forming properties, and is not flowed or removed by sweat or sebum, that is, is free from cosmetic crumbling.

By virtue of these advantages, the cosmetic composition of the present invention finds wide applications in various foundations, makeup cosmetics (such as eye shadow, eyeliner, eyebrow pencil, mascara and nail enamel), skin cosmetics (such as pack, lipstick, rouge and sun screen), hair cosmetics, medical cosmetics and the like.

Among them, especially preferred are nail enamels, mascaras, eye shadows, foundations and packs.

In the manufacture of nail enamels or mascaras, it is preferred to incorporate the aqueous polymer emulsion in amounts (as a solid content) from 1 to 60 wt %, preferably from 10 to 50 wt %, and particularly from 30 to 50 wt % based on the total weight of the composition, and the humectant in amounts from 0.01 to 10 wt %, preferably 0.1 to 5 wt % based on the total weight of the composition.

In the manufacture of foundations or eye shadows, it is preferred to incorporate the aqueous polymer emulsion in amounts (as a solid content) from 1 to 30 wt %, preferably from 1 to 15 wt % based on the total weight of the composition, and the humectant in amounts from 0.01 to 30 wt %, preferably 0.1 to 10 wt % based on the total weight of the composition.

In the manufacture of packs, it is preferred to incorporate the aqueous polymer emulsion in amounts (as a solid content) from 20 to 50 wt %, preferably from 30 to 40 wt % based on the total weight of the composition, and the humectant in amounts from 0.01 to 10 wt %, preferably 0.5 to 10 wt % based on the total weight of the composition.

PREFERRED EMBODIMENTS OF THE INVENTION

Having generally described this invention, a further understanding can be obtained by reference to certain specific examples which are provided herein for purposes of illustration only and are not intended to be limiting unless otherwise specified.

EMULSION EXAMPLES (Production of aqueous polymer emulsions)

Hereinbelow, "parts" means "parts by weight", and "%" means "% by weight".

Emulsion Example 1

A reactor is equipped with an agitator, a reflux condenser, a dropping funnel, a thermometer and a nitrogen introduction tube. 150 parts of water, 3 parts of sodium lauryl sulfate and 0.5 part of potassium persulfate are charged into the reactor. Nitrogen gas is passed through the contents of the reactor to remove any oxygen dissolved in the contents. Then, 78 parts of styrene, 22 parts of 2-ethylhexyl acrylate, 10 parts of butylcarbitol acetate and 2.0 parts of n-dodecyl mercaptan are put in the dropping funnel.

The temperature of the reactor is elevated to 70° C., and the monomer-containing contents of the dropping funnel are added dropwise, with stirring, over a period of 3 hours. After the dropwise addition, the resultant reaction mixture is aged for 3 hours. Thereafter, some aggregates are removed to obtain an emulsion having a solid content of 45%.

The thus obtained emulsion contained a copolymer, which had a glass transition temperature (Tg) of 52° C. as measured using DSC and had a weight average molecular weight (Mw) of 28,000 as measured by GPC (reference: polystyrene).

4 parts of dibutyl phthalate was added to 100 parts of the above emulsion, and agitated for 30 minutes by means of a disperser, thereby obtaining an aqueous polymer emulsion (1) having a solid content of 43%.

Emulsion Example 2

Charged into the reactor as used in Example 1 are 150 parts of water, 3.0 parts of polyoxyethylene nonylphenyl ether, 0.5 part of potassium persulfate, 98 parts of isobutyl methacrylate, 2 parts of hydroxyethyl methacrylate, 10 parts of acetyltriethyl citrate, 13 parts of carbitol and 2.5 parts of n-dodecyl mercaptan. Nitrogen gas is then passed through the contents of the reactor to remove any oxygen dissolved in the contents.

The temperature of the contents of the reactor is elevated to 70° C. with stirring, and polymerization is performed over a period of 3 hours. The resultant reaction mixture is aged for 3 hours at the same temperature. Thereafter, some aggregates are removed to obtain an aqueous polymer emulsion (2) having a solid content of 44%.

The thus obtained aqueous polymer emulsion is subjected to the same measurements as in Example 1. The emulsion contained a copolymer, with a glass transition temperature (Tg) of 60° C. and a weight average molecular weight (Mw) of 32,000.

Emulsion Example 3

Charged into the reactor as used in Referential Example 1 are 150 parts of water, 2.0 parts of sodium dodecylbenzenesulfonate, 0.5 part of ammonium persulfate, 55 parts of methyl methacrylate, 33 parts of n-butyl acrylate, 10 parts of styrene, 2 parts of acrylic acid, 5 parts of dibutyl phthalate and 2.5 parts of n-dodecyl mercaptan. Nitrogen gas is passed through the contents of the reactor to remove any oxygen dissolved in the contents.

The temperature of the contents of the reactor is elevated to 70° C. with stirring, and polymerization is performed over a period of 3 hours. The resultant reaction mixture is aged for 3 hours at the same temperature. Thereafter, some aggregates are removed to obtain an emulsion having a solid content of 41%.

The thus obtained emulsion is subjected to the same measurements as in Example 1. The emulsion contained a copolymer, with a glass transition temperature (Tg) of 30° C. and a weight average molecular weight (Mw) of 28,000.

15 parts of butyl cellosolve is added to 100 parts of the above emulsion, and agitated for 30 minutes by means of a disperser, thereby obtaining an aqueous polymer emulsion (3) having a solid content of 36%.

Emulsion Example 4

Charged into the reactor as used in Referential Example 1 are 150 parts of water, 0.5 part of sodium polyoxyethylene lauryl ether sulfate, 0.5 part of potassium persulfate, 63 parts of methyl methacrylate, 21 parts of 2-ethylhexyl acrylate, 10.0 parts of styrene, 3 parts of hydroxyethyl methacrylate, 3 parts of acrylic acid, 10 parts of diisobutyl adipate and 2.5 parts of n-dodecyl mercaptan.

The mixture is then treated as in Example 3.

After the resultant reaction mixture is aged for 3 hours at the same temperature, some aggregates are removed to obtain an emulsion having a solid content of 46%.

The thus obtained emulsion is subjected to the same measurements as in Example 1. The emulsion contained a copolymer, having a glass transition temperature (Tg) of 52° C. and a weight average molecular weight (Mw) of 32,000.

15 parts of diethylcarbitol is added to 100 parts of the above emulsion, and agitated for 30 minutes by means of a disperser, thereby obtaining an aqueous polymer emulsion (4) having a solid content of 40%.

Emulsion Example 5

Charged into the reactor as used in Referential Example 1 are 150 parts of water, 0.5 part of sodium polyoxyethylene lauryl ether sulfate, 0.5 part of ammonium persulfate, 60 parts of methyl methacrylate, 25 parts of 2-ethylhexyl acrylate, 10.0 parts of styrene, 3 parts of hydroxyethyl methacrylate, 2 parts of acrylic acid, 10 parts of diisobutyl adipate and 2.5 parts of n-dodecyl mercaptan.

The mixture is treated as in Example 3.

After the resultant reaction mixture is aged for 3 hours at the same temperature, some aggregates are removed to obtain an emulsion having a solid content of 45%.

The thus obtained emulsion is subjected to the same measurements as in Example 1. The emulsion contained a copolymer, having a glass transition temperature (Tg) of 45° C. and a weight average molecular weight (Mw) of 32,000.

20 parts of dimethylcarbitol is added to 100 parts of the above emulsion, and agitated for 30 minutes by means of a disperser, thereby obtaining an aqueous polymer emulsion (5) having a solid content of 37.5%.

Emulsion Example 6

Charged into the reactor as used in Referential Example 1 are 125 parts of water, 3.0 parts of sodium lauryl sulfate, 0.5 part of ammonium persulfate, 73 parts of styrene, 27 parts of 2-ethylhexyl acrylate, 7.0 parts of dibutyl phthalate, 15 parts of butyl cellosolve, and 1.0 part of butyl mercaptan.

The mixture is treated as in Example 3.

After the resultant reaction mixture is aged for 3 hours at the same temperature, some aggregates are removed to obtain an aqueous polymer emulsion (6) having a solid content of 47%.

The thus obtained aqueous polymer emulsion is subjected to the same measurements as in Example 1. The emulsion contained a copolymer, having a glass transition temperature (Tg) of 40° C. and a weight average molecular weight (Mw) of 57,000.

Emulsion Example 7 (Comparative)

Charged into the reactor as used in Referential Example 1 are 125 parts of water, 3.0 parts of sodium lauryl sulfate, 0.5 part of ammonium persulfate, 73 parts of styrene, 27 parts of 2-ethylhexyl acrylate, and 1.0 part of butyl mercaptan.

The mixture is treated as in Example 3.

After the resultant reaction mixture is aged for 3 hours at the same temperature, some aggregates were removed to obtain an emulsion having a solid content of 47%.

The thus obtained emulsion is subjected to the same measurements as in Example 1. The emulsion contained a copolymer, having a glass transition temperature (Tg) of 40° C. and a weight average molecular weight (Mw) of 57,000.

Dibutyl phthalate and butyl cellosolve are then added to the above emulsion in amounts of 7 parts and 15 parts, respectively, per 100 parts of the monomer contained in the emulsion, and agitated for 30 minutes by means of a disperser, thereby obtaining an aqueous polymer emulsion (7) having a solid content of 42.6%.

Cosmetic Example 1 (Eye Shadow)

An eye shadow of the following formulation is prepared by the below described procedure.
Formulation:

| Component | Parts by weight |
| --- | --- |
| microcrystalline wax | 3.0 |
| stearic acid | 3.0 |
| liquid paraffin | 8.5 |
| lanolin | 1.0 |
| sorbitan monostearate | 1.5 |
| glycerol | 5.5 |

-continued

| Component | Parts by weight |
| --- | --- |
| triethanolamine | 1.5 |
| methyl cellulose | 0.5 |
| aqueous polymer emulsion (1) | 10.0 |
| pearl pigment | 10.0 |
| ultramarine blue | 2.0 |
| ion exchange water | balance |
| perfume | trace |
| antiseptic | trace |

Procedure:

Methyl cellulose, glycerol and triethanolamine are dissolved in ion exchange water, and heated. Subsequently, pearl pigment and ultramarine blue are uniformly dispersed in the solution, thereby obtaining an aqueous phase dispersion. Then, oil phase components including microcrystalline wax are heated so as to obtain a solution, and this solution is added to the above aqueous phase dispersion under agitation to effect emulsification. The resultant emulsion is cooled, and the aqueous polymer emulsion (1), perfume and antiseptic are added to the cooled emulsion. Thus, a blue creamy eye shadow is obtained.

The thus obtained eye shadow exhibited excellent gloss and water (sweat) repellency.

Cosmetic Example 2 (Mascara)

A mascara of the following formulation is prepared by the below described procedure.

| Formulation: | |
| --- | --- |
| Component | Parts by weight |
| aqueous polymer emulsion (2) | 45.0 |
| black iron oxide | 15.0 |
| talc | 10.0 |
| methyl hydroxypropyl cellulose | 2.0 |
| polyoxyethylene sorbitan monooleate | 1.5 |
| glycerol | 5.0 |
| ion exchange water | balance |
| perfume | trace |
| antiseptic | trace |

Procedure:

Methyl hydroxypropyl cellulose, talc and aqueous polymer emulsion (2) are added to ion exchange water, and uniformly blended under agitation. Subsequently, a color paste comprised of black iron oxide, glycerol and polyoxyethylene sorbitan monooleate is added, and uniformly blended. Further, the perfume and antiseptic are added to obtain a black mascara.

The thus obtained mascara exhibited excellent gloss and water (sweat) repellency.

Cosmetic Example 3 (Eyeliner)

A liquid, film-forming type eyeliner of the following formulation was prepared by the below described procedure.

| Formulation: | |
| --- | --- |
| Component | Parts by weight |
| aqueous polymer emulsion (3) | 58.0 |
| carbon black | 6.0 |
| titanium dioxide | 3.0 |

-continued

Formulation:

| Component | Parts by weight |
| --- | --- |
| polyoxyethylene sorbitan monostearate | 1.0 |
| glycerol | 3.0 |
| methyl cellulose | 1.0 |
| ion exchange water | balance |
| perfume | trace |
| antiseptic | trace |

Procedure:

Polyoxyethylene sorbitan monostearate is dissolved in ion exchange water to obtain a solution. Carbon black and titanium oxide are blended into the solution, and uniformly dispersed by the use of a colloid mill. Glycerol, methyl cellulose and aqueous polymer emulsion (3) are added to the dispersion, and uniformly blended. Finally, the perfume and antiseptic are added, thereby obtaining a black, film-forming type eyeliner.

The thus obtained eyeliner exhibited excellent gloss and water (sweat) repellency.

Cosmetic Examples 4–6 and Comparative Cosmetic Example 1 (Nail Enamel)

Nail enamels of the formulations shown in Table 1 are prepared according to the following procedure.

Procedure:

The pigment is dispersed in ion exchange water, and then, aqueous polymer emulsions (4)–(7) and other components are added to the dispersion. The resultant mixture is uniformly blended under agitation, and degassed, thereby obtaining an aqueous nail enamel.

The thus obtained nail enamels are evaluated with respect to (a) adhesion, (b) water repellency and (c) abrasion resistance according to the following methods and criteria:

Evaluation Method (a) Adhesion

The nail enamel is applied to the nail with a nailbrush or the like under the conditions such that the ambient temperature and relative humidity were 25° C. and 60%, respectively, and dried to obtain a film on the surface of the nail. 30 minutes later, the film is scraped with a microspatula, and the scraping degree (resistance to scraping) is visually inspected.

(b) Water repellency

The nail enamel is uniformly applied to a nylon plate of 0.5×15×40 mm with a nail enamel brush, and dried for one hour under the conditions such that the ambient temperature and relative humidity were 25° C. and 60%, respectively, thereby obtaining a film on the surface of the plate. Subsequently, the film-containing plate is immersed in water of 35° C. for one hour, and the degradation degree (resistance to degradation, e.g., clouding, swelling, softening, peeling, etc.) of the film is visually checked.

(c) Abrasion resistance

The above-mentioned 30 min. dried film is rubbed with a cotton cloth 50 times, and the degree of abrasion (resistance to abrasion) is visually inspected.

The evaluation results are also shown in Table 1.

TABLE 1

| Formulation (percentages by weight) | | Example 4 | Example 5 | Example 6 | Comparative Example 1 |
| --- | --- | --- | --- | --- | --- |
| aqueous polymer emulsion (4) | | 86.6% | — | — | — |
| aqueous polymer emulsion (5) | | — | 92.4% | — | — |
| aqueous polymer emulsion (6) | | — | — | 73.7% | — |
| aqueous polymer emulsion (7) | | — | — | — | 81.2% |
| pigment (red pigment C.I. 73360) | | 1.6 | 1.6 | 1.6 | 1.6 |
| methyl cellulose | | 0.5 | 0.5 | 0.5 | 0.5 |
| ion exchange water | | balance | balance | balance | balance |
| perfume | | 0.1 | 0.1 | 0.1 | 0.1 |
| antiseptic | | 0.1 | 0.1 | 0.1 | 0.1 |
| silicone anti-foaming agent | | 0.1 | 0.1 | 0.1 | 0.1 |
| evaluated items/ results | (a) adhesion | ⊚ | ⊚ | ⊚ | x |
| | (b) water repellency | ⊚ | ⊚ | ⊚ | ▲ |
| | (c) abrasion resistance | ⊚ | o | o | ▲ |

Evaluation Criteria:
⊚: excellent
o: good
▲: fair
x: poor.

As apparent from the results of Table 1, the cosmetic compositions according to the present invention are superior to the comparative cosmetic composition.

Cosmetic Example 7 (Creamy Foundation)

Ingredients (1) to (4) were blended, to which ingredient (5) was added for dispersion, and while stirring, a mixture of ingredients (6) to (9) was slowly added thereto for emulsification to obtain a creamy foundation.

| | |
| --- | --- |
| (1) Polyether modified silicone (SH3775C)*) | 2.0 wt % |
| (2) Dimethylpolysiloxane (50 cs) | 10.0 |
| (3) Octamethyl cyclotetrasiloxane | 8.0 |
| (4) Perfume | 0.2 |
| (5) Silicone-treated cosmetic powder**) | 15.0 |
| (6) Glycerol | 5.0 |
| (7) Magnesium sulfate | 1.0 |
| (8) Aqueous polymer emulsion (1) | 7.0 |
| (9) Purified water | balance |

*): Product of Shin-etsu Silicone Co., Ltd.
**): The silicone-treated cosmetic powder was prepared by blending the following ingredients, added with 2% by weight of methylhydrogen polysiloxane (product of Shin-etsu Silicone Co., Ltd., KF99), and subjected to a heat treatment.

| | |
| --- | --- |
| Titanium oxide | 8% by weight |
| Talc | 4 |
| Red iron oxide | 1.2 |
| Iron (III) oxide | 2.6 |
| Iron (II) oxide | 0.2 |

Cosmetic Example 8 (Facial Pack)

A facial pack having the following formulation was prepared.

| | |
|---|---|
| Aqueous polymer emulsion (2) | 70 wt % |
| Polyethylene glycol 4000 | 2 |
| polyoxyethylene methylglucoside (20 EO adduct)[1] | 3 |
| Xanthan gum | 0.5 |
| Squalane | 3 |
| Ethanol | 7.7 |
| Perfume | 0.5 |
| Preservative | suitable amount |
| Sorbitan monostearate[2] | 0.5 |
| polyoxyethylene sorbitan monostearate[3] (20 EO adduct) | 0.2 |
| Water | balance |
| Total | 100 wt % | note:
[1] GlucamE-20 ® (product of Amerchol Corp.)
[2] Rheodol SPS10 ® (product of Kao Corporation)
[3] Rheodol TWS120 ® (product of Kao Corporation)

What is claimed is:

1. A method of manicuring or pedicuring, which comprises applying to a nail a nail enamel composition, the nail enamel composition comprising:

(i) a pigment; and (ii) an aqueous polymer emulsion in an mount, as a solid content, of from 1 to 60% by weight based on the total weight of the nail enamel composition, said aqueous polymer emulsion being produced by polymerizing at least one polymerizable monomer having a double bond in the presence of a plasticizer or film-forming auxiliary selected from the group consisting of cellosolves carbitols, acetates, alcohols, diols, esters, ethers and diethylbenzene, and in which the plasticizer or film-forming auxiliary is not removed from the emulsion except for any plasticizer or film forming auxiliary, if any, present in aggregates which may optionally be removed.

2. The method according to claim 1, wherein said monomer is a compound selected from the group consisting of ethylenically unsaturated carboxylic acids, hydroxyl group-containing ethylenic monomers, ethylenic amides, ethylenic amines and salts thereof, aromatic mono- and di-vinyl compounds, acrylates, methacrylates, vinyl cyanide compounds, vinyl esters, vinyl halides, ethylenically unsaturated fluoromonomers and ethylenically unsaturated silicone macromonomers.

3. The method according to claim 1, wherein said plasticizer or film-forming auxiliary is added in an amount of from 1 to 50 parts by weight per 100 parts by weight of the monomer.

4. The method according to claim 1, wherein said plasticizer or film-forming auxiliary is added in an amount of from 5 to 30 parts by weight per 100 parts by weight of the monomer.

5. The method according to claim 1, wherein the polymerization of the monomer is conducted in the presence of surfactant.

6. The method according to claim 5, wherein the surfactant is present in an amount of no more than 5 parts by weight per 100 parts by weight of the monomer.

7. The method according to claim 1, wherein said polymer has a weight average molecular weight of 200,000 or less.

8. The method according to claim 1, wherein said polymer has a weight average molecular weight of from 10,000 to 100,000.

9. The method according to claim 1, wherein said aqueous polymer emulsion is produced by polymerizing a mixture of at least one hydrophilic monomer with at least one hydrophobic monomer in the presence of said plasticizer or film-forming auxiliary said hydrophilic monomer being selected from the group consisting of ethylenically unsaturated carboxylic acids, hydroxyl group-containing ethylenic monomers, ethylenic amides, and amines and salts thereof, and said hydrophobic monomer being selected from the group consisting of aromatic mono- and di-vinyl compounds, acrylates, methacrylates, vinyl cyanides, vinyl esters, vinyl halides, ethylenically unsaturated fluoromonomers, and ethylenically unsaturated silicone macromonomers.

10. The method according to claim 9, wherein said mixture comprises 0.01 to 30% of said hydrophilic monomer and 70 to 99.99% of said hydrophobic monomer.

11. The method according to claim 1, wherein after the polymerization of the monomer, additional plasticizer or film-forming auxiliary is added.

12. The method of claim 1, wherein said pigment is selected from the group consisting of CI 12120, CI 73360, CI 74160, CI 11680, titanium dioxide, brown iron oxide, red iron oxide, mica titanium, and bismuth oxychloride.

13. The method of claim 1, wherein said pigment is selected from the group consisting of CI 12120, CI 73360, CI 74160 and CI 11680.

14. The method of claim 1, wherein said nail enamel composition further comprises a humectant.

15. The method of claim 1, wherein said nail enamel composition further comprises a dispersant for the pigment.

16. A method of claim 1, wherein said nail enamel composition further comprises a thickener.

* * * * *